United States Patent [19]

Ueda et al.

[11] 4,235,813
[45] Nov. 25, 1980

[54] AROMATIC SULFONAMIDE SULFONYL CHLORIDE COMPOUNDS

[75] Inventors: Hideo Ueda; Hiroshi Sawaguchi, both of Odawara, Japan

[73] Assignee: Fuji Photo Film Co., Ltd., Minami-ashigara, Japan

[21] Appl. No.: 23,502

[22] Filed: Mar. 23, 1979

Related U.S. Application Data

[62] Division of Ser. No. 868,164, Jan. 9, 1978, Pat. No. 4,176,134.

[30] Foreign Application Priority Data

Jan. 11, 1977 [JP] Japan .................................. 52/1797

[51] Int. Cl.³ .......................................... C07C 143/70
[52] U.S. Cl. .............................. 260/543 R; 430/223; 260/198
[58] Field of Search ........ 260/543 R, 556 AR, 556 S; 96/56.6, 77; 430/223

[56] References Cited

U.S. PATENT DOCUMENTS

| | | | |
|---|---|---|---|
| 2,362,598 | 11/1944 | Vittum et al. .......................... | 96/56.6 |
| 3,942,987 | 3/1976 | Landholm et al. ...................... | 96/3 |
| 4,042,393 | 8/1977 | Wada et al. ............................ | 96/56.6 |

FOREIGN PATENT DOCUMENTS

802654 10/1958 United Kingdom ................ 260/543 R

*Primary Examiner*—Natalie Trousof
*Assistant Examiner*—L. Hendriksen
*Attorney, Agent, or Firm*—Sughrue, Rothwell, Mion, Zinn and Macpeak

[57] ABSTRACT

An aromatic sulfonamide sulfonyl chloride, useful as an intermediate in the preparation of cyan dye-releasing redox compounds for diffusion transfer photographic materials, represented by the following general formula (I)

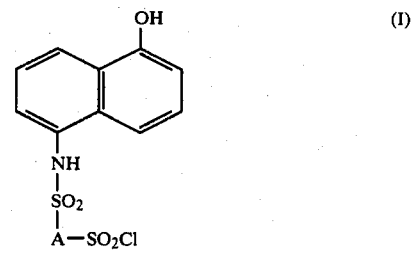

wherein A represents a divalent benzene nucleus or a divalent naphthalene nucleus, in which in each nucleus the bonding thereto is symmetrical, and a method for the synthesis thereof comprising reacting an aromatic disulfonyl chloride represented by the formula (IIa) or (IIb)

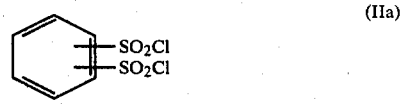

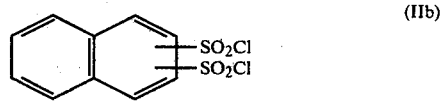

wherein the two sulfonyl chloride groups are substituted at symmetrical positions on the benzene and the naphthylene ring, with 5-amino-1-naphthol.

3 Claims, 4 Drawing Figures

AROMATIC SULFONAMIDE SULFONYL CHLORIDE COMPOUNDS

This is a division of application Ser. No. 868,164, filed Jan. 9, 1978, now U.S. Pat. No. 4,176,134.

BACKGROUND OF THE INVENTION

1. Field of the Invention

This invention related to aromatic sulfonamide sulfonyl chloride compounds and to a method for the synthesis thereof, which aromatic sulfonamide sulfonyl fluoride compounds are useful as intermediates in the synthesis of cyan dye-releasing redox compounds used in diffusion transfer photographic materials.

2. Description of the Prior Art

Japanese Patent Publication No. 126331/1974, British Pat. No. 1,458,471, U.S. Pat. No. 3,929,760, and U.S. Pat. No. 3,942,987 discloses that an aromatic sulfonamide sulfonyl fluoride having the formula (IV) below can be selectively synthesized by the reaction between benzene sulfonyl chloride sulfonyl fluoride and 5-amino-1-naphthol in accordance with the following:

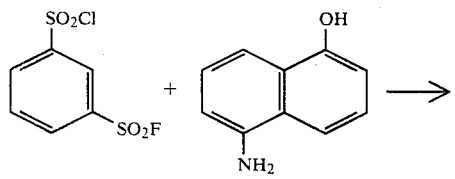

(III)  5-Amino-1-naphthol

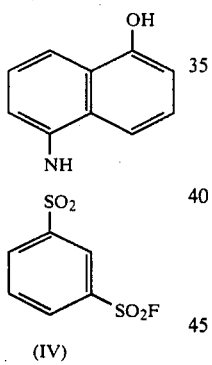

(IV)

whereby an asymmetric disulfonamide linkage results. However, this method involves various drawbacks in terms of pollution and manufacturing procedures. Further, the resulting fluorine-containing compound (IV) has insufficient reactivity.

Introduction of an aniline moiety into one of the sulfonyl chloride groups of naphthalene disulfonyl chloride compounds wherein two disulfonyl chloride groups are present in symmetrical positions of the naphthalene nucleus is described in *J. Prakt. Chem.*, 117, 77 (1927), but this process gives rise to only a small amount of the desired compound and the resulting product obtained is a mixture of various compounds.

SUMMARY OF THE INVENTION

Accordingly, a principal object of the present invention is to provide compounds useful as intermediates for cyan dye-releasing redox compounds for use in diffusion transfer photographic materials.

A further object of this invention is to provide an efficient method of synthesis of compounds useful as intermediates to prepare cyan dye-releasing redox compounds.

Another object of the present invention is to provide a method for producing aromatic, asymmetric disulfonamide compounds without any environment problems and without using materials such as those liberating fluoride ion corrosive to the equipment used.

Still another object of the present invention is to provide a method for synthesizing intermediate compounds useful for cyan dye-releasing redox compounds for diffusion transfer photographic materials involving as few synthetic steps as possible based on readily available starting materials.

It has now been found as a result of extensive studies that aromatic sulfonamide sulfonyl chloride compounds represented by the general formula (I)

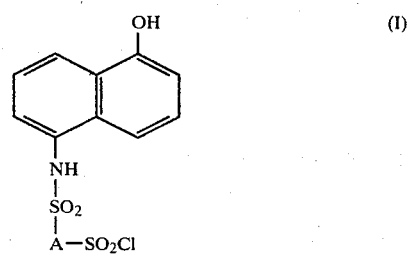

wherein A represents a divalent benzene nucleus or a divalent naphthylene nucleus, in which in each nucleus the bonding thereto is symmetrical can be obtained by reacting an aromatic disulfonyl chloride represented by the formula (IIa) or (IIb)

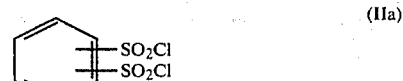

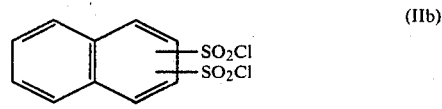

wherein the two sulfonyl chloride groups are substituted at symmetrical positions on the benzene and the naphthylene ring with 5-amino-1-naphthol and further that the resulting compounds represented by the general formula (I) above achieve the above-described various objects.

DETAILED DESCRIPTION OF THE INVENTION

Figure 1:
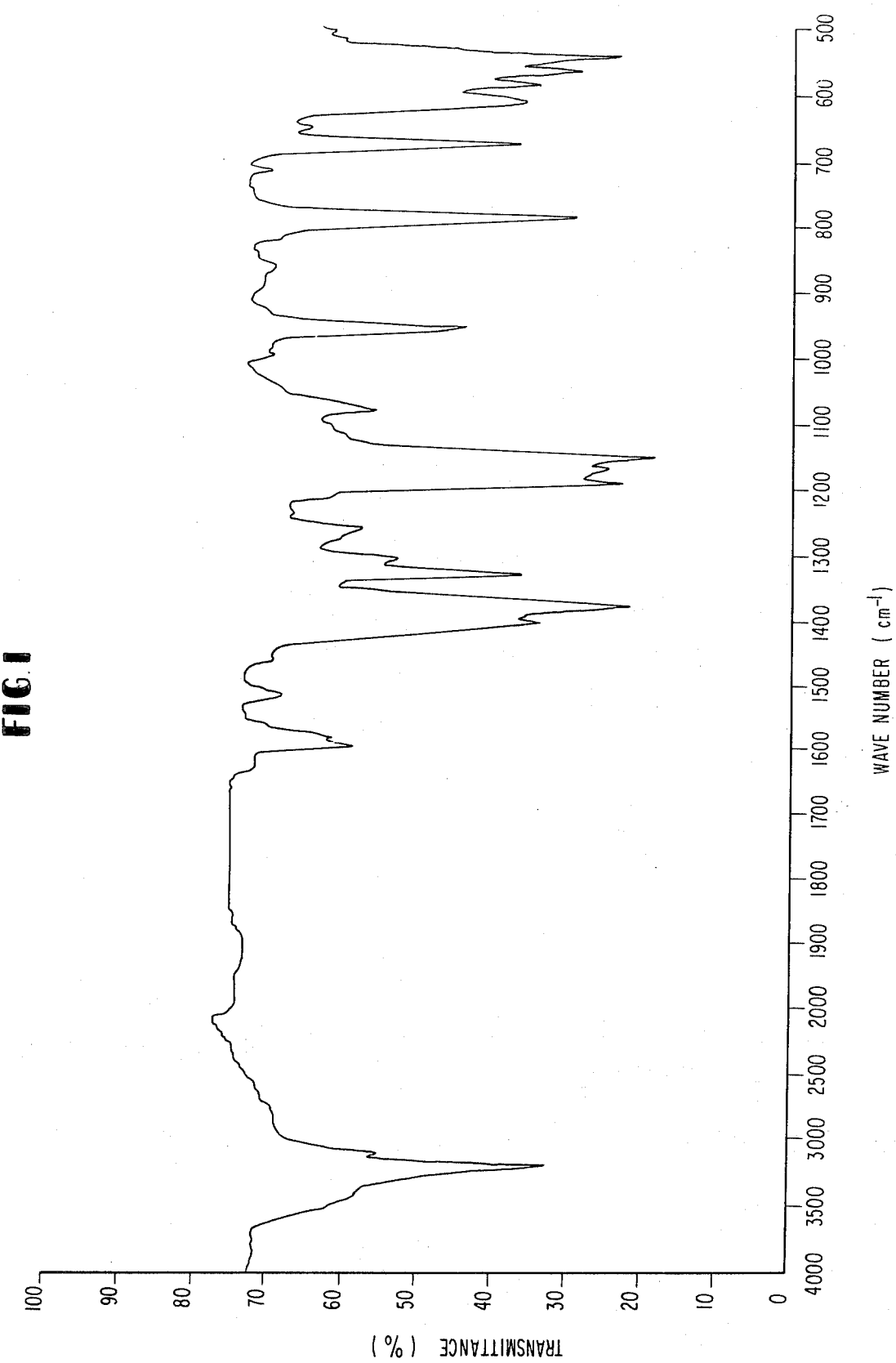
FIGS. 1 to 4 illustrate, respectively, the IR absorption spectra of Compound (I-1) to (I-4) of the present invention.

Of the compounds represented by the general formula (I) above aromatic sulfonamide sulfonyl chlorides in which A is a 1,3-divalent benzene nucleus, a 1,5-divalent naphthalene nucleus, a 2,6-divalent naphthalene nucleus or a 2,7-divalent naphthalene nucleus are preferred and it has been found that compounds represented by the general formula (I) where A is either a 1,3-divalent benzene nucleus or a 2,7-divalent naphthalene nucleus can be particularly advantageously produced by the method of the present invention with a high practical feasibility as well as with a high synthetic yield.

In the synthesis of the compounds of this invention, it has been found that the selectivity of the reaction can be markedly increased by the following improvement; first, careful and gradual (little by little) addition of an acid eliminating agent; second, selection of a solvent system which allows the acid eliminating agent to function rather slowly; and third, the use of an weak acid eliminating agent. Consequently, compounds such as Compound (I-1), 3-(5'-hydroxynaphthylaminosulfonyl)-benzene sulfonyl chloride, in the following reaction schematic

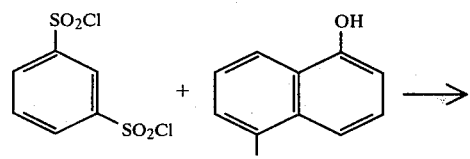

(II-1)   5-Amino-1-naphthol

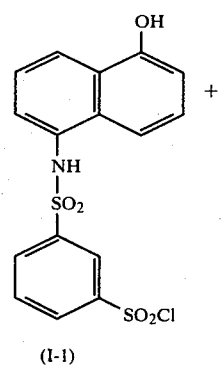

(I-1)

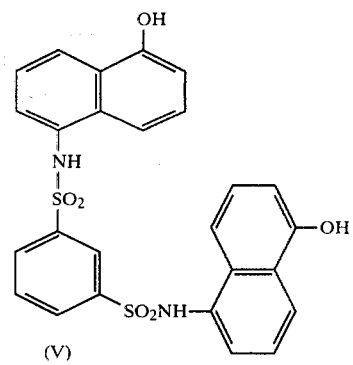

(V)

can be obtained with a much higher yield than would have been expected, while, due to the improved reaction selectivity, the formation of biproduct compounds, such as Compound (V), benzene-m-disulfonylamino-(5-hydroxy)naphthalene, is effectively suppressed.

The selectivity of this reaction critically depends on whether 5-amino-1-naphthol will react with, e.g., benzene-m-disulfonyl chloride (II-1) to produce Compound (I-1), or whether the 5-amino-1-naphthol will condense with the already formed Compound (I-1) to produce the bisamide Compound (V). It is thus surprising that the synthesis of Compound (I-1) with a high degree of selectivity has been successful.

Further, it has been proved that the method of the present invention can be effectively applied to disulfonyl chlorides other than benzene-m-disulfonyl chloride (II-1) described above as being representative in this invention, such as naphthalene-1,5-disulfonyl chloride, naphthalene-2,6-disulfonyl chloride, naphthalene-2,7-disulfonyl chloride and other aromatic disulfonyl chlorides.

Starting with any of the resulting compounds prepared by the above-described procedures, one can obtain a cyan dye-releasing redox compounds (VII) useful for diffusion transfer photographic materials in the following series of reaction schematics, again using benzene-m-disulfonyl chloride (II-1) as a representative aromatic disulfonyl chloride starting material.

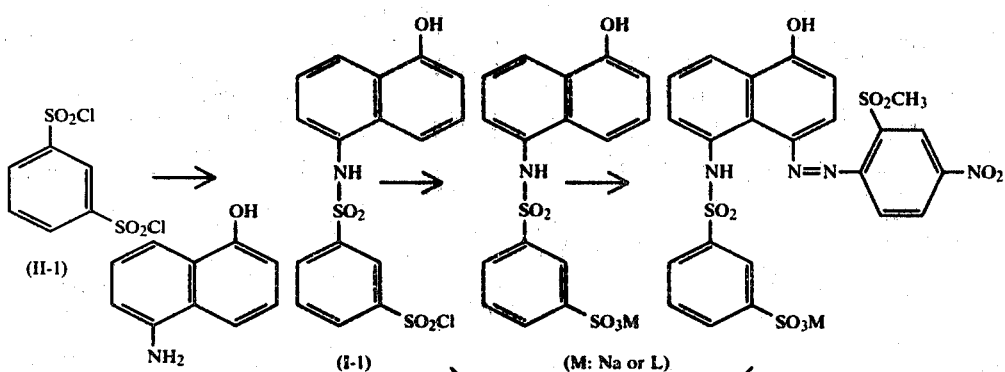
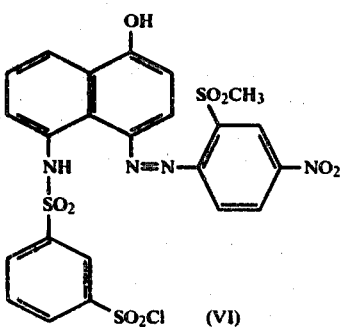
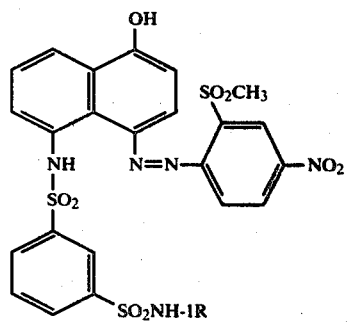
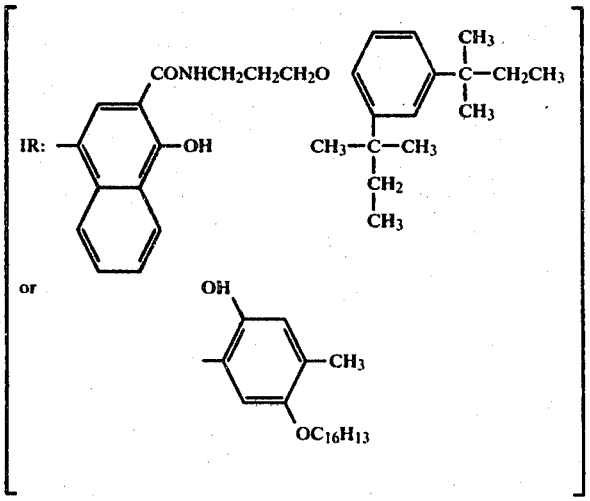
First, Compound (I-1) is azo coupled to provide an intermediate azo dye (VI), or Compound (I-1) is hydro- The cyan dye-releasing redox compounds which can be prepared in accordance with these procedures exhibit excellent performance similar to those prepared using conventional methods.

The aromatic disulfonyl chlorides used as starting materials in preparing the compounds of the general formula (I) in this invention can be represented by the formula (IIa) or (IIb)

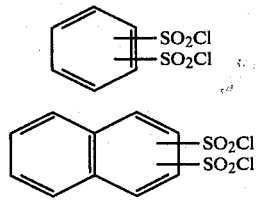

wherein the two sulfonyl chloride groups are substituted as symmetrical positions on the benzene and the naphthylene ring. Preferred examples of the aromatic disulfonyl chlorides as starting materials are those substituted in the 1,3-positions of a benzene nucleus, the 1,5-positions of a naphthalene nucleus, the 2,6-positions of a naphthalene nucleus and the 2,7-positions of a naphthalene nucleus, and a particularly preferred example is that substituted in the 1,3-positions of a benzene nucleus.

Any of the following reaction conditions may be employed, depending on the need involved, for the reaction between an aromatic disulfonyl chloride as defined above and 5-amino-1-naphthol.

(1) A molar ratio of about 0.5 to about 2.0 mole of the aromatic disulfonyl chloride per mole of 5-amino-1-naphthol (2) Reaction, optionally, under an inert gas atmosphere such as an atmosphere of nitrogen, helium, etc.

(3) Reaction carried out around room temperature (15°–30° C.).
(The reaction can also be conducted at an elevated temperature between about 30° and about 150° C., or under cooling between about 15° and about −10° C.)

(4) Use of agitation (5) Use of a solvent and acid eliminating agent during the reaction (6) Reaction under a dry atmosphere (Practically, moisture can be removed from the solvent and the reagents using a calcium chloride desiccant tube or by heating.)

These aromatic disulfonyl chlorides used as a starting material in the process of this invention can be prepared by reacting the corresponding aromatic sodium disulfonates with thionyl chloride or phosphorus chloride. For example, the reaction of sodium benzene-m-disulfonate or sodium naphthalene-1,5-disulfonate with thionyl chloride results in the production of benzene-m-disulfonyl chloride or naphthalene-1,5-disulfonyl chloride, respectively, as described in greater detail in Synthesis Examples 1 and 2, given hereinafter. Other benzene- or naphthalene-disulfonyl chlorides used as starting materials can be prepared likewise from the corresponding sodium benzene- or naphthalene-disulfonates.

Aromatic sodium disulfonates and 5-amino-1-naphthol are commercially available and in addition the syntheses thereof are described in, for example, "The Merck Index", "Organic Synthesis", etc.

Suitable solvents which can be used for the reaction include any solvent or solvents capable of dissolving the starting material used, for example, hydrocarbons (e.g., hexane, ligroin, decalin, etc.), halogenated hydrocarbons (e.g., dichloromethane, carbon tetrachloride, dichloroethane, trichloroethylene, etc.), ethers (e.g., diethyl ether, tetrahydrofuran, anisole, etc.), aromatic hydrocarbons (e.g., benzene, toluene, xylene, ethylbenzene, etc.), N-alkyllactams (e.g., N-methylpyrrolidone), esters (e.g., ethyl acetate), ketones (e.g., acetone, methyl ethyl ketone, methyl isobutyl ketone, etc.), carboxylic acids (e.g., formic acid, glacial acetic acid, propionic acid, etc.), acetonitrile, carbon disulfide, nitrobenzene, halogenated benzenes (e.g., chlorobenzene, dichlorobenzene, etc.), alcohols (e.g., methanol, ethanol, isopropanol, etc.), etc. Generally, a suitable amount of the solvent ranges from about 5 to about 20 times by volume to the amount of the aromatic disulfonyl chloride used.

One or two of these solvents can be chosen, considering the reaction conditions to be used, solvent characteristics including boiling point, solubility, reactivity, odor, etc., and also economic factors.

In some cases, an acid eliminating agent can be used in an excess amount and such then also functions as solvent, simultaneously. However, it is preferred to use a solvent as described above since the excess acid eliminating agent tends to hydrolyze SO$_2$Cl groups. The reaction will also proceed even when the acid eliminating agent is not present in the reaction system since 5-amino-1-naphthol also functions as acid eliminating agent. However, it is preferred to use an acid eliminating agent since the reaction proceeds better and further when the 5-amino-1-naphthol functions as an acid eliminating agent some of the starting material useful in the reaction with the aromatic disulfonyl chloride is diverted to an alternative use.

The acid eliminating agent, which comprises organic or inorganic bases, is preferably used to promote the reaction. A suitable amount of the acid eliminating agent is about 0.5 to about 2 mols per mol of the aromatic disulfonyl chloride. The acid eliminating agent can be used as a solution or dispersion thereof in a solvent, generally as a dispersion especially when the agent is an inorganic compound. Suitable specific examples of acid eliminating agents which can be used are weakly basic compounds as described hereinafter.

Suitable organic bases which can be used as acid eliminating agents include pyridine and alkylpyridines (e.g., α-picoline, 2,6-dimethylpyridine, etc.), quinoline and alkylquinolines (e.g., quinaldine, lepidine, etc.), dialkylanilines (e.g., dimethylaniline, diethylaniline, etc.), trialkylamines (e.g., trimethylamine, triethylamine, tri-n-propylamine, etc.), triethylenediamine, nitrogen-containing heterocyclic compounds (e.g., imidazole, etc.), etc. Suitable inorganic bases which can be used as acid eliminating agents include potassium acetate, sodium acetate, sodium bicarbonate, potassium bicarbonate, sodium carbonate, potassium carbonate, calcium carbonate, sodium hydroxide, potassium hydroxide, etc. One or more of these bases as described above can be used.

Several examples of compounds produced by the present invention are illustrated below.

Compound (I-1)

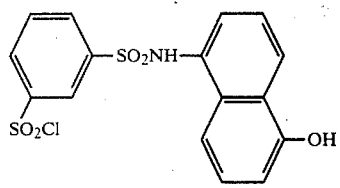

3-(5'-Hydroxynaphthylaminosulfonyl)benzene-sulfonyl chloride
m.p. 162°–164° C.

Compound (I-2)

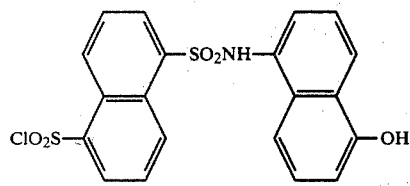

5-(5'-Hydroxynaphthylaminosulfonyl)naphthalene-1-sulfonyl chloride
m.p. 161°–165° C.

Compound (I-3)

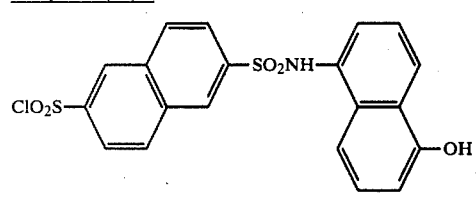

6-(5'-Hydroxynaphthylaminosulfonyl)naphthalene-2-sulfonyl chloride
m.p. 223°–226° C.

Compound (I-4)

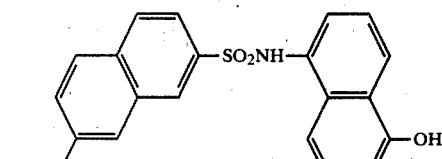

7-(5'-Hydroxynaphthylaminosulfonyl)naphthalene-2-sulfonyl chloride
m.p. 187° C. (decomposes)

The syntheses of the starting materials used and several compounds of the general formula (I) of the present invention are given below. Unless otherwise indicated herein, all parts, percents, ratios and the like are by weight.

PREPARATION EXAMPLE 1

Preparation of Benzene-m-Disulfonyl Chloride 90 g (0.3 mol) of sodium benzene-m-disulfonate, 210 ml of thionyl chloride and 6 ml of dimethylformamide were placed in a 500 ml flask, and the mixture was heated in an oil bath for 4 hours under refluxing. After distilling off any excess of the thionyl chloride, the reaction mixture was poured into 300 ml of ice-water and extracted with 300 ml of benzene. The extract was dried over anhydrous sodium sulfate and concentrated under reduced pressure. 300 ml of n-hexane was added to the resulting oily substance followed by stirring to precipitate crystals as a product. The resulting product was then distilled at 163°–167° C./8.5 mmHg to obtain the desired product as crystals having a melting point of 58°–59° C. Yield; 67%.

PREPARATION EXAMPLE 2

Preparation of Naphthalene-1,5-Disulfonyl Chloride 110 g (0.33 mol) of sodium metal, 1 l of benzene, 100 ml of thionyl chloride and 20 ml of dimethylformamide were placed in a 2 l flask, and the mixture was heated in an oil bath for 4 hours under refluxing. After allowing the reaction mixture to cool, 7 l of ice-water was added thereto. The benzene layer was separated, dried and concentration under reduced pressure. The resulting crystals were recovered by suction filtration to obtain the desired product as crystals having a melting point of 186°–188° C. Yield; 94%.

EXAMPLE 1

[Synthesis of Compound (I-1)]

In a 500 ml flask were charged 14 g (0.05 mole) of benzene-m-disulfonyl chloride and 100 ml of glacial acetic acid. Into this solution a mixture comprising 8 g of 5-amino-naphthol (0.05 mole), 100 ml of glacial acetic acid and 50 ml of methyl ethyl ketone was added dropwise over a 30 minute period at room temperature. Next, 7 g (0.025 mole) of benzene-m-disulfonyl chloride and then 4.1 g (0.05 mole) of sodium acetate were added and the reaction was conducted for one hour. The reaction mixture was poured into 1.6 liters of ice water under agitation. Consequently, a black oily product formed, which crystallized when allowed to stand for 3 hours. The crystals were separated by means of an aspirating filter, and dissolved in 80 ml of methylene chloride. The solution was then filtered, and to the filtrate was added 200 ml of n-hexane to again separate out crystals. The recrystallized product obtained had a melting point of 162°–164° C., weighed 8.3 g corresponding to a 42% yield.

| Elemental analysis for $C_{16}H_{12}O_5N_1S_1Cl_1$ | | | | |
|---|---|---|---|---|
| | C | H | N | Cl |
| Calculated (%) | 48.30 | 3.04 | 3.52 | 8.91 |
| Found (%) | 48.74 | 3.02 | 3.55 | 9.20 |

Compounds (I-1) to (I-4) each was analyzed by N.M.R. and IR spectral analysis. The N.M.R. analysis was carried out in $CD_3COCD_3$ using an N.M.R. instrument R-20 (60 MHz), a product of Hitachi-Perkin Elmer Co.

Figure 2:
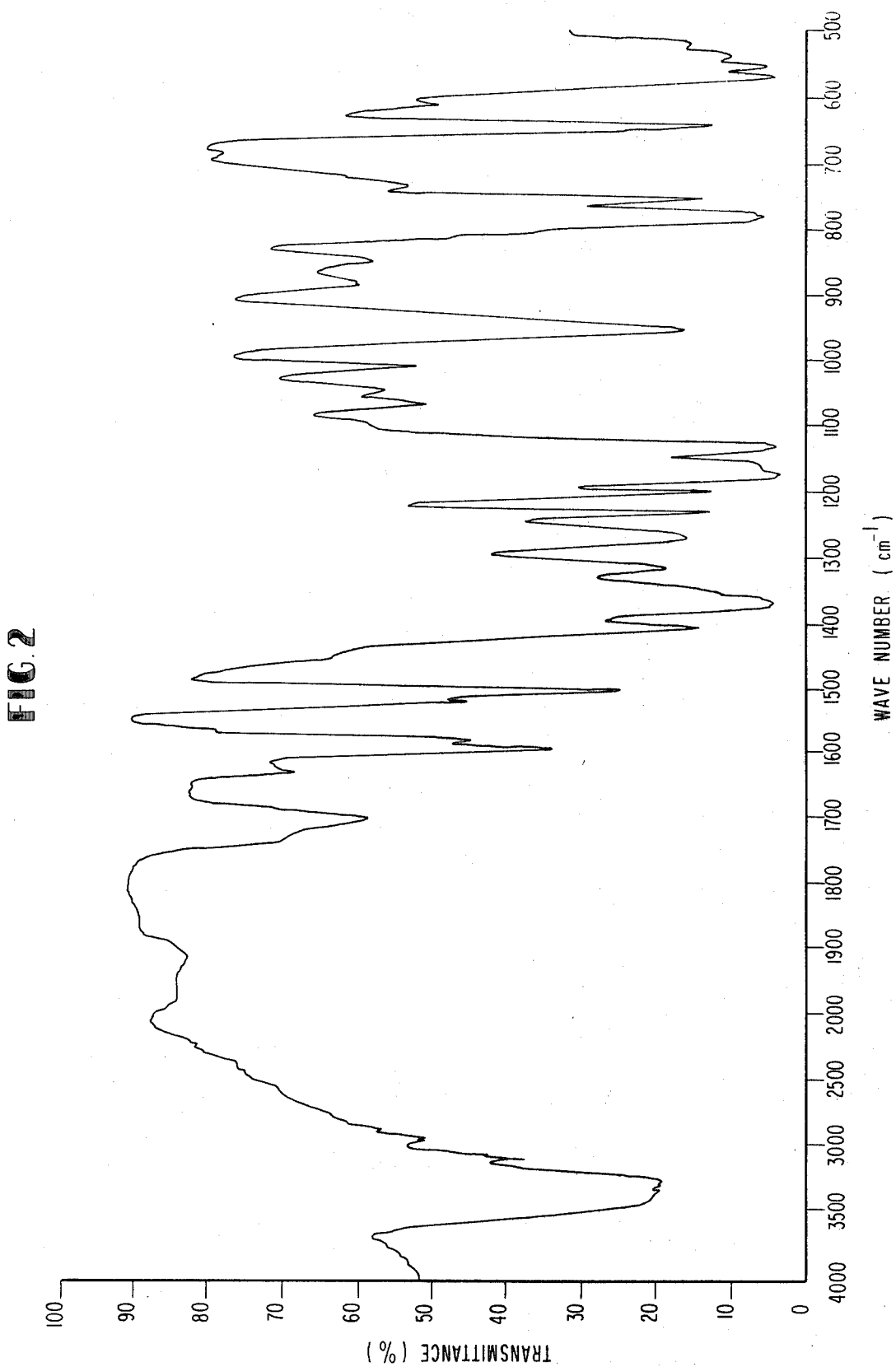
Figure 3:
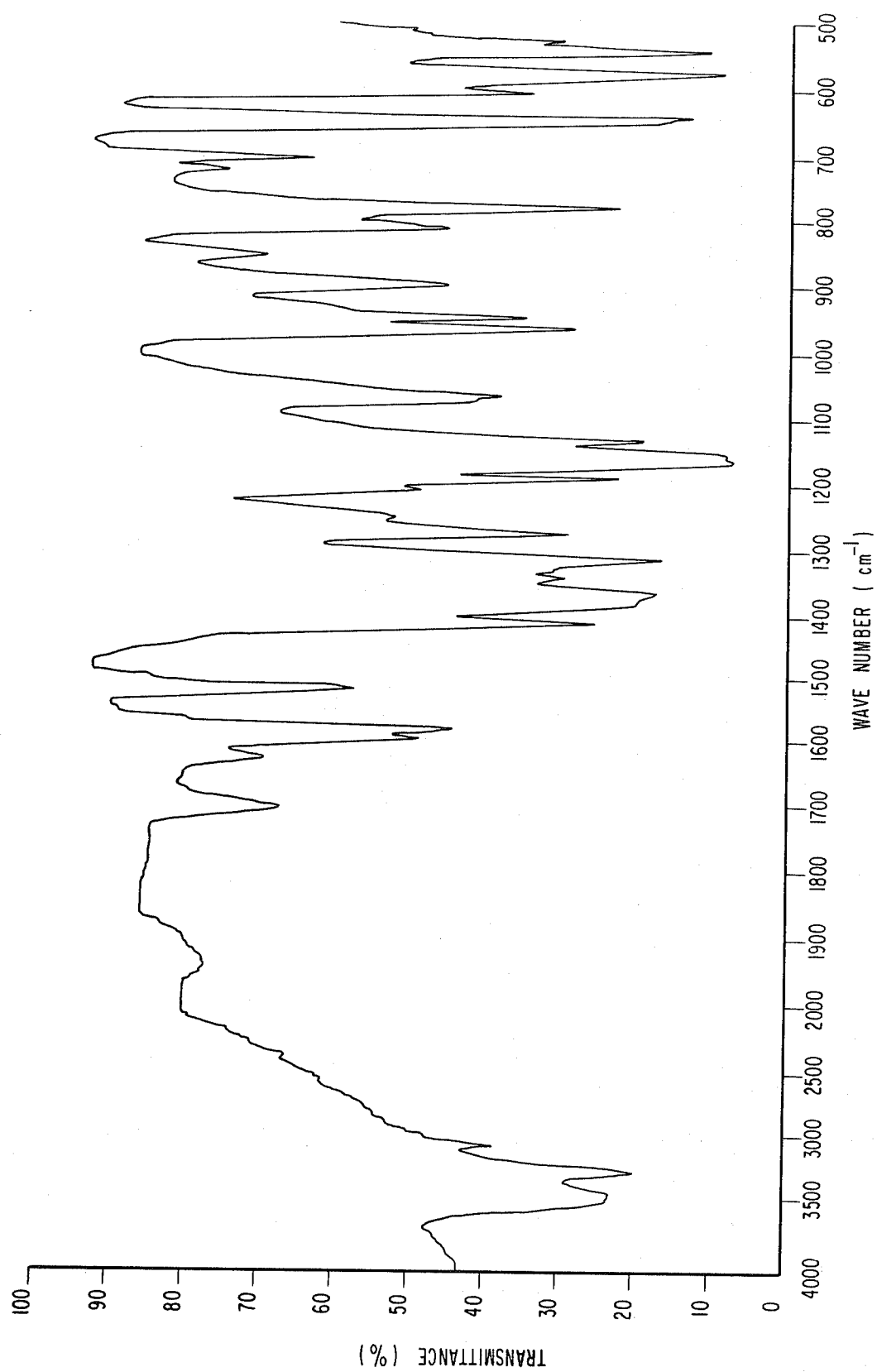
Figure 4:
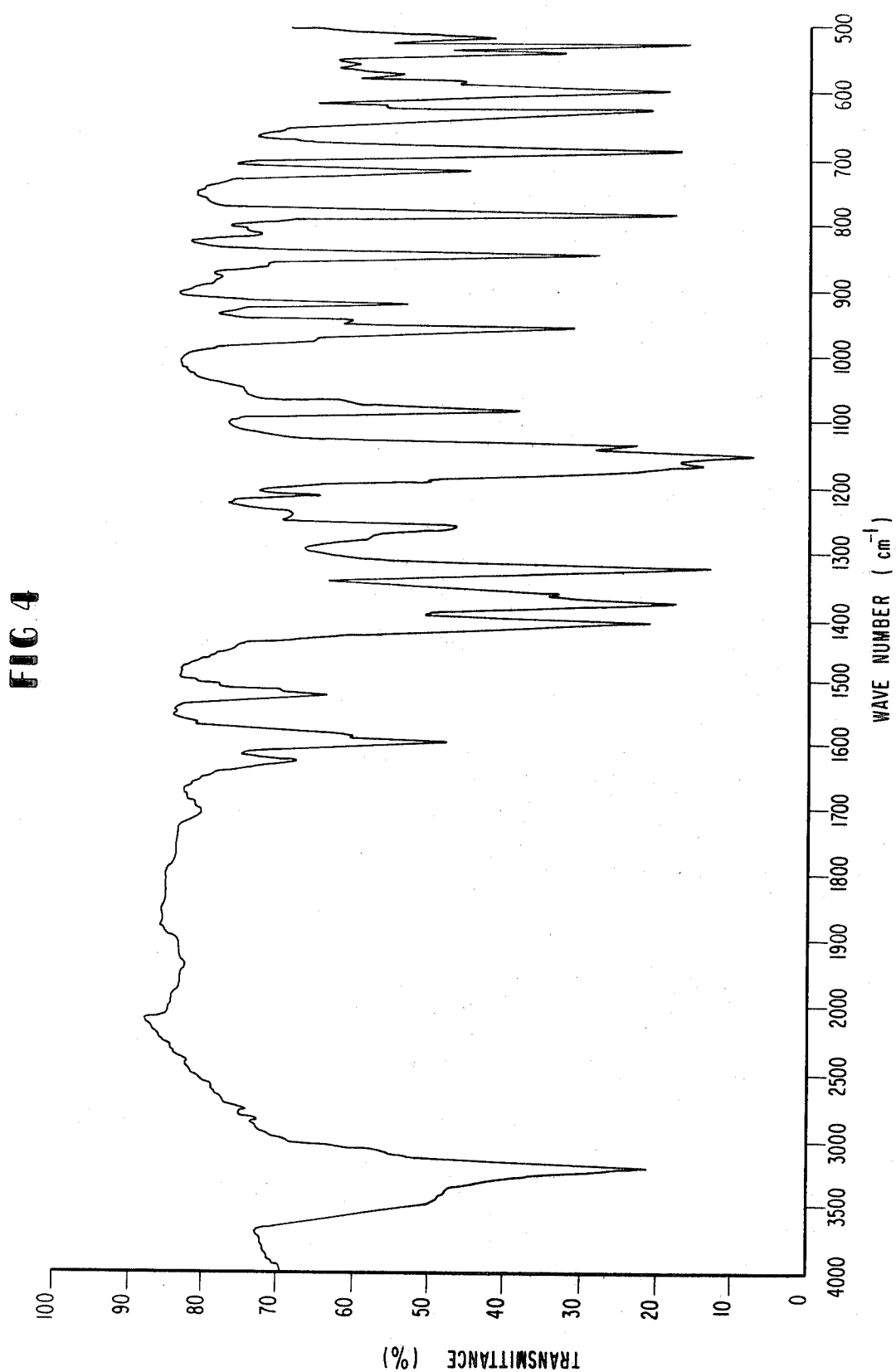

The IR spectrum for each of Compounds (I-1) to (I-4) is shown in FIGS. 1 to 4 respectively of the accompanying drawings.

The result of N.M.R. analysis:

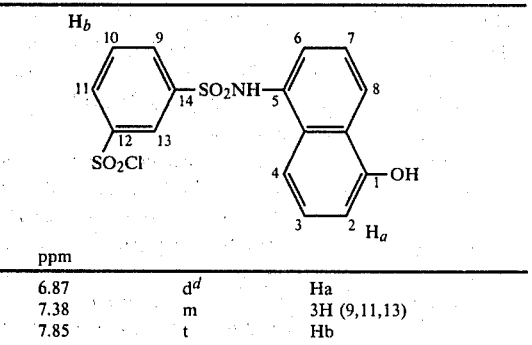

| ppm | | |
|---|---|---|
| 6.87 | $d^d$ | Ha |
| 7.38 | m | 3H (9,11,13) |
| 7.85 | t | Hb |
| 8.25 | m | 5H (3,4,6,7,8) |

-continued

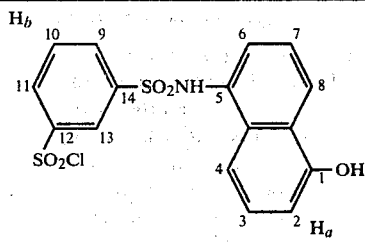

| ppm | | |
|---|---|---|
| 9.28 | s | NHSO$_2$ or OH |

IR spectral analysis was carried out using an IR Spectrometer IR-G available from JASCO Co., using the potassium bromide tablet method.

From the results of the above described analysis, all of the products synthesized in Example 1 to 5 given herein were strictly confirmed to be represented by the chemical structures given for Compounds (I-1) to (I-4) hereinbefore in this specification.

EXAMPLE 2

Compound (I-1) was also prepared in an alternative manner. 66 g (0.24 mole) of benzene-m-disulfonyl chloride and 200 ml of acetone were placed in a 500 ml three-necked flask and dissolved with stirring. The mixture was cooled to a temperature below 7° C. in an ice-water bath, and 40.3 g (0.48 mole) of sodium bicarbonate was added to the mixture. Then, 31.8 g (0.20 mole) of 5-amino-1-naphthol was added to the mixture is seven portions over a period of 30 minutes and the resulting mixture was allowed to react at a temperature below 7° C. for 2 hours. 2 g of activated carbon was added to the mixture which was then suction filtered. The filtrate was poured into 500 ml of ice-water and the precipitated crystals were recovered by filtration. The crystals were dissolved in 150 ml of methylene chloride and 750 ml of n-hexane was added to the solution to precipitate the desired product to obtain 52 g of Compound (I-1) having a melting point of 161°–164° C. as crystals. Yield, 61%.

EXAMPLE 3

[Synthesis of Compound (I-2)]

In a 500 ml three-necked flask were charged 18 g (0.05 mole) of naphthalene-1,5-disulfonyl chloride dissolved in 100 ml of acetone, to which were added 8 g (0.05 mole) of 5-amino-1-naphthol, 6.5 g (0.05 mole) of quinoline and 50 ml of tetrahydrofuran over a 20 minute period. The reaction was then conducted for 2 hours at 45° C. To the reaction mixture were added further 200 ml of ethyl acetate and 200 ml of a 5% dilute aqueous hydrochloric acid solution whereby the contents separated into two layers. The organic layer was condensed under reduced pressure, after being dried with sodium sulfate. The product was dissolved in 20 ml of ethyl acetate and again separated in a purified form by the addition of 300 ml of benzene. The resulting crystals of Compound (I-2) amounted to 10.5 g corresponding to a yield of 47%. The melting point of Compound (I-2) was 161°–165° C.

| Elemental analysis for C$_{20}$H$_{14}$O$_5$N$_1$S$_2$Cl$_1$ | | | | |
|---|---|---|---|---|
| | C | H | N | Cl |
| Calculated (%) | 53.63 | 3.15 | 3.13 | 7.92 |
| Found (%) | 53.40 | 3.00 | 3.22 | 8.25 |

The results of N.M.R. analysis:

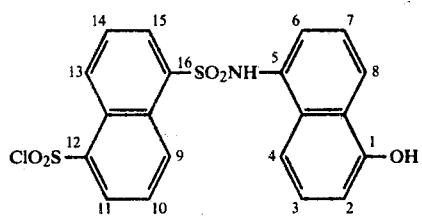

| ppm | | |
|---|---|---|
| 6.76 | d$^m$ | H |
| 7.05 | d | H$_6$ |
| 7.30 | 2H | (3,7) |
| 7.90 | 2H | (14,15) |
| 8.40 | 4H | (4,8,10,11) |
| 9.03 | d$^m$ | H$_{13}$ |
| 9.32 | d$^m$ | H$_9$ |
| 9.03 } | | |
| 9.40 | | OH or NHSO$_2$ |

EXAMPLE 4

[Synthesis of Compound (I-3)]

A 200 ml flask was charged with 4.2 g (0.013 mole) of naphthalene-2,6-disulfonyl chloride and 50 ml of acetone. To this solution were added dropwise 1.6 g (0.010 mole) of 5-amino-1-naphthol, 1.0 g (0.013 mole) of α-picoline, 24 ml of acetonitrile and 4 ml of glacial acetic acid over a period of 45 minutes at 50°–60° C. The flask was kept at 50°–70° C. for one hour and 20 minutes for exhaustive reaction. Then the reaction mixture was poured into 500 ml of ice water whereby a crystalline product formed, which was collected by suction filtration. The crystals thus obtained were purified by dissolving them in ethyl acetate and recrystallizing therefrom by addition of benzene to the solution in an amount of about 3 times the volume of the ethyl acetate. 1.6 g of Compound (I-3) in crystalline form with a melting point (223°–226° C. was obtained. The yield was 36%.

| Elemental analysis for C$_{20}$H$_{14}$O$_5$N$_1$S$_2$Cl$_1$ | | | | |
|---|---|---|---|---|
| | C | H | N | Cl |
| Calculated (%) | 53.63 | 3.15 | 3.13 | 7.92 |
| Found (%) | 53.92 | 3.20 | 3.24 | 7.56 |

The result of N.M.R. analysis:

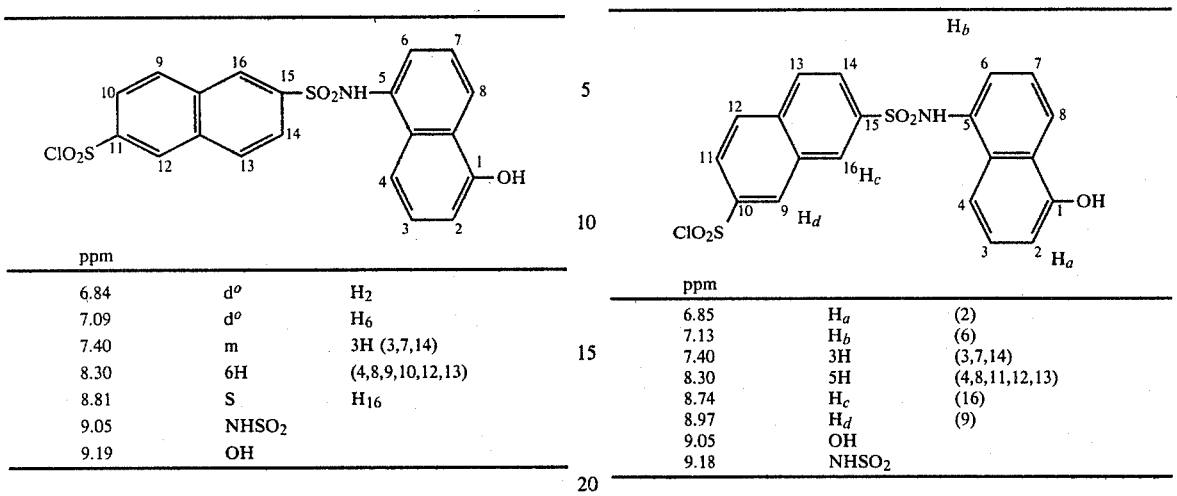

| ppm | | |
|---|---|---|
| 6.84 | d° | H₂ |
| 7.09 | d° | H₆ |
| 7.40 | m | 3H (3,7,14) |
| 8.30 | 6H | (4,8,9,10,12,13) |
| 8.81 | s | H₁₆ |
| 9.05 | NHSO₂ | |
| 9.19 | OH | |

EXAMPLE 5

[Synthesis of Compound (I-4)]

A 200 ml flask was charged with 4.2 g (0.013 mole) of naphthalene-2,7-disulfonyl chloride and 20 ml of acetone, to which 1.6 g (0.010 mole) of 5-amino-1-naphthol, 24 ml of acetonitrile and 4 ml of glacial acetic acid were added over a period of 30 minutes at room temperature. One hour was allowed for reaction. Then 1.0 g (0.013 mole) of pyridine was added over a period of 10 minutes, and further the reaction was continued for 30 minutes. After the addition of 50 ml of methylene chloride, the reaction mixture was washed with a 5% aqueous hydrogen chloride solution. The organic phase mainly comprising methylene chloride was dried with sodium sulfate and condensed. A crystalline product was deposited on addition of n-hexane. By purifying the product through recrystallization, 2.6 g of the final product was obtained which had a melting (decomposition) point of 187° C. and which was represented by the formula given hereinbefore for Compound (I-4). The yield was 59%.

| Elemental anaylsis for $C_{20}H_{14}O_5N_1S_2Cl_1$ | | | | |
|---|---|---|---|---|
| | C | H | N | Cl |
| Calculated (%) | 53.63 | 3.15 | 3.13 | 7.92 |
| Found (%) | 53.63 | 3.28 | 3.19 | 8.32 |

The results of N.M.R. analysis:

| ppm | | |
|---|---|---|
| 6.85 | H$_a$ | (2) |
| 7.13 | H$_b$ | (6) |
| 7.40 | 3H | (3,7,14) |
| 8.30 | 5H | (4,8,11,12,13) |
| 8.74 | H$_c$ | (16) |
| 8.97 | H$_d$ | (9) |
| 9.05 | OH | |
| 9.18 | NHSO₂ | |

While the invention has been described in detail and with reference to specific embodiments thereof, it will be apparent to one skilled in the art that various changes and modifications can be made therein without departing from the spirit and scope thereof.

What is claimed is:

1. An aromatic sulfonamide sulfonyl chloride compound represented by the following general formula (I)

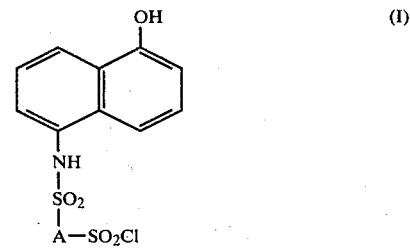

wherein A represents a divalent naphthalene nucleus, in which in each nucleus the bonding thereto is symmetrical.

2. The aromatic sulfonamide sulfonyl chloride compound of claim 1, wherein A is a 1,5-divalent naphthalene nucleus, a 2,6-divalent naphthalene nucleus or a 2,7-divalent naphthalene nucleus.

3. The aromatic sulfonamide sulfonyl chloride compound of claim 1, wherein said compound represented by the general formula (I) is 5-(5'-hydroxynaphthylaminosulfonyl)-naphthalene-1-sulfonyl chloride, 6-(5'-hydroxynaphthylaminosulfonyl)naphthalene-2-sulfonyl chloride or 7-(5'-hydroxynaphthylaminosulfonyl)naphthalene-2-sulfonyl chloride.

* * * * *